United States Patent
Balbierz et al.

[19]

[11] Patent Number: 5,964,744
[45] Date of Patent: Oct. 12, 1999

[54] POLYMERIC MEDICAL DEVICE SYSTEMS HAVING SHAPE MEMORY

[75] Inventors: Daniel J. Balbierz, San Carlos; Jack M. Walker, Portola Valley; Joseph R. Thomas, San Carlos; Robert S. Bley, Menlo Park; Kevin Van Bladel, Mountain View, all of Calif.

[73] Assignee: Menlo Care, Inc., Menlo Park, Calif.

[21] Appl. No.: 08/316,933

[22] Filed: Oct. 3, 1994

Related U.S. Application Data

[63] Continuation-in-part of application No. 08/000,274, Jan. 4, 1993, Pat. No. 5,599,291.

[51] Int. Cl.⁶ .................................................. A61M 25/00
[52] U.S. Cl. ............................................ 604/530; 606/198
[58] Field of Search ........................... 604/8, 9, 10, 175, 604/204, 283, 96; 623/5

[56] References Cited

U.S. PATENT DOCUMENTS

| | | | |
|---|---|---|---|
| 5,171,318 | 12/1992 | Gibson et al. | 623/5 |
| 5,348,537 | 9/1994 | Wiesner et al. | 604/96 |

OTHER PUBLICATIONS

"Kingston Technologies: A Brief Description of the Company, Its Products and Technology", Jun. 1989.
"Hypan" from "Hydrogels: Specilaty Plastic for Biomedical, Pharmaceutical and Industrial Applications", by Vladimir Stoy, Apr. 1990.

*Primary Examiner*—Wynn Wood Coggins
*Assistant Examiner*—A. T. Nguyen
*Attorney, Agent, or Firm*—Joseph F. Shirtz

[57] ABSTRACT

In accordance with the invention, there are provided medical devices with incorporated shape memory systems that allow a polymeric medical device to be inserted in a first conformation or configuration and revert to a second conformation or configuration. The invention is useful in allowing the easy insertion or implantation of a device followed by expansion of the device in order to be retained without expulsion from a body cavity, for example. In another aspect of the invention there is provided a medical device, such as a ureteral stent, that includes comprising an elongated member having a proximal end portion and a distal end portion joined by a body portion. The elongated member has an initial outer diameter. A retention construction serves for retaining the member within a bodily cavity. The member is formulated of a physiologically acceptable polymer capable of hydrating and expanding from the initial member outer diameter to form a final member outer diameter. The device can assume differing shapes and can exhibit different degrees of softening at different places along its length and possess shape memory so that it can be inserted in a first conformation or configuration and revert to a second conformation or configuration upon the occurrence of a triggering event such as hydration.

11 Claims, 10 Drawing Sheets

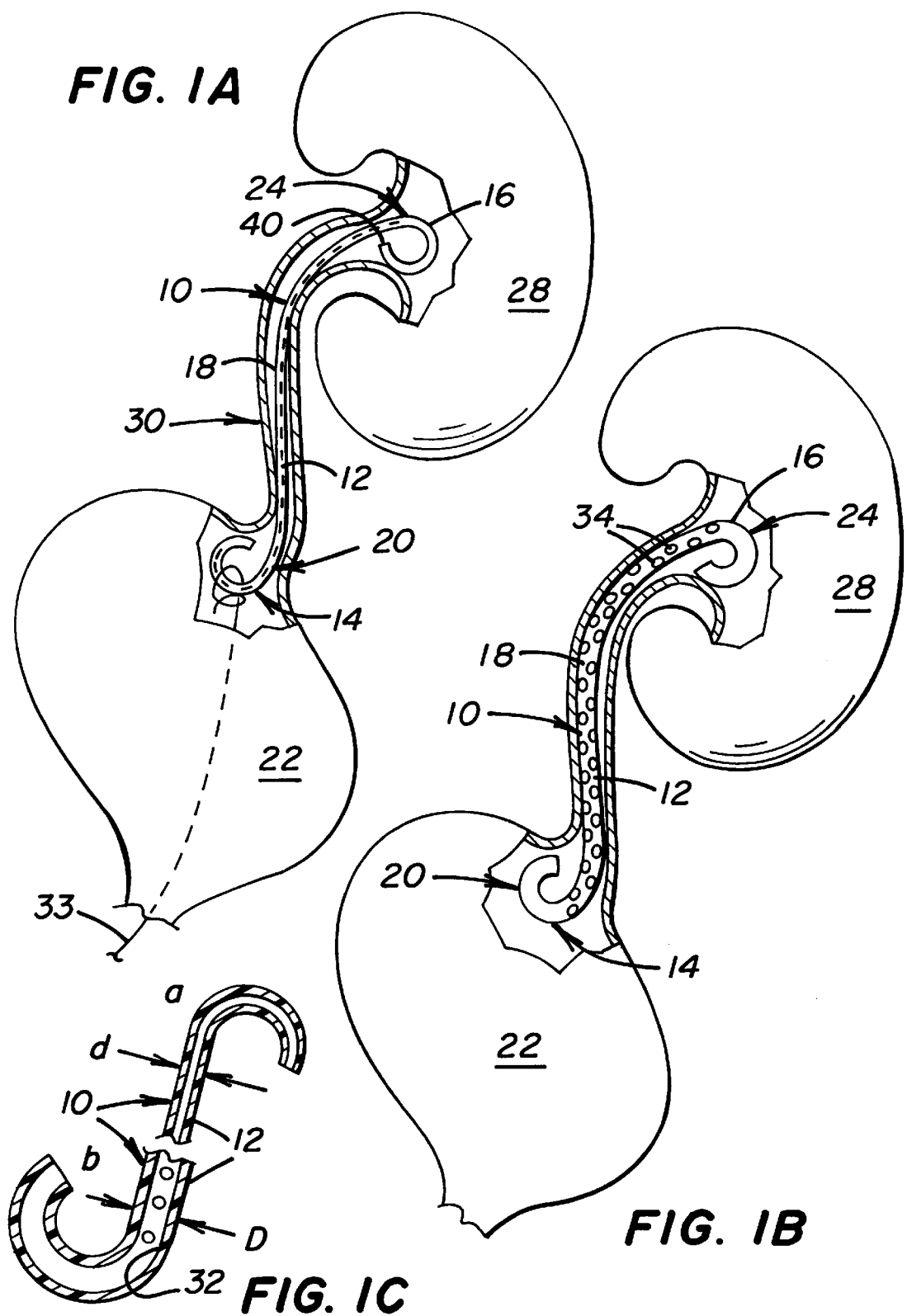

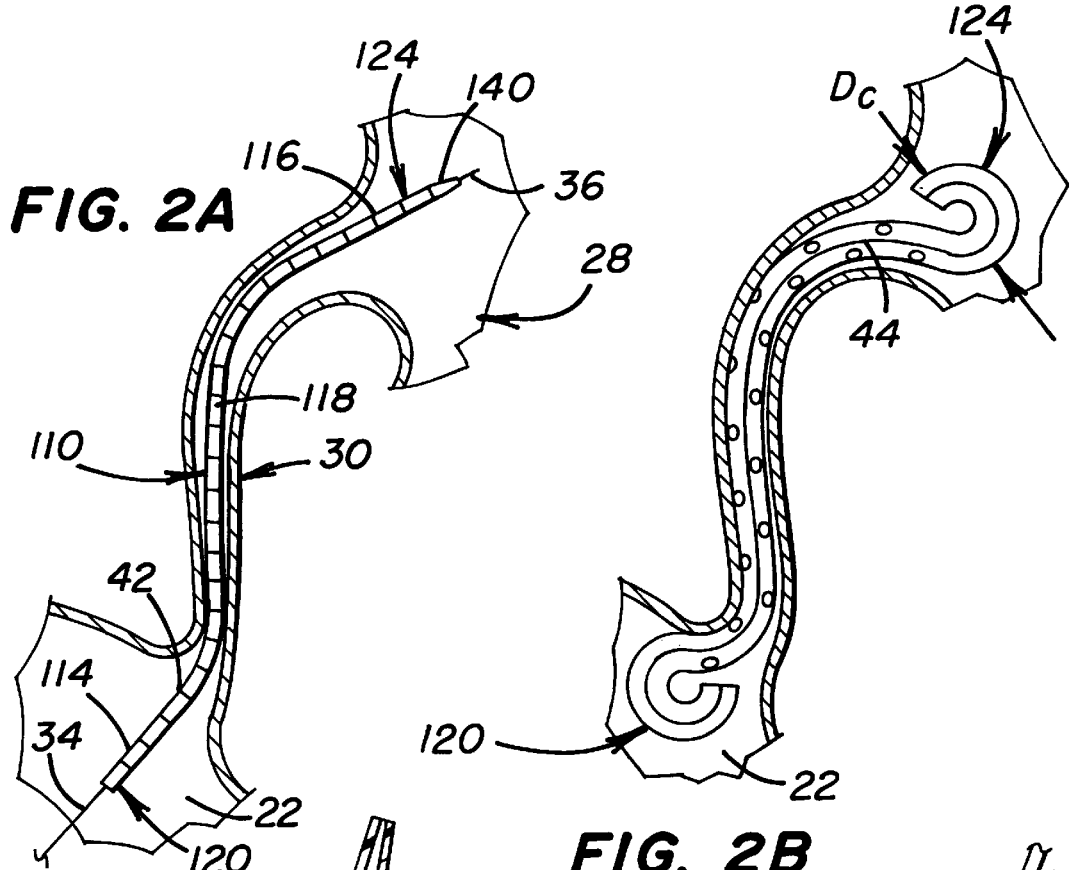
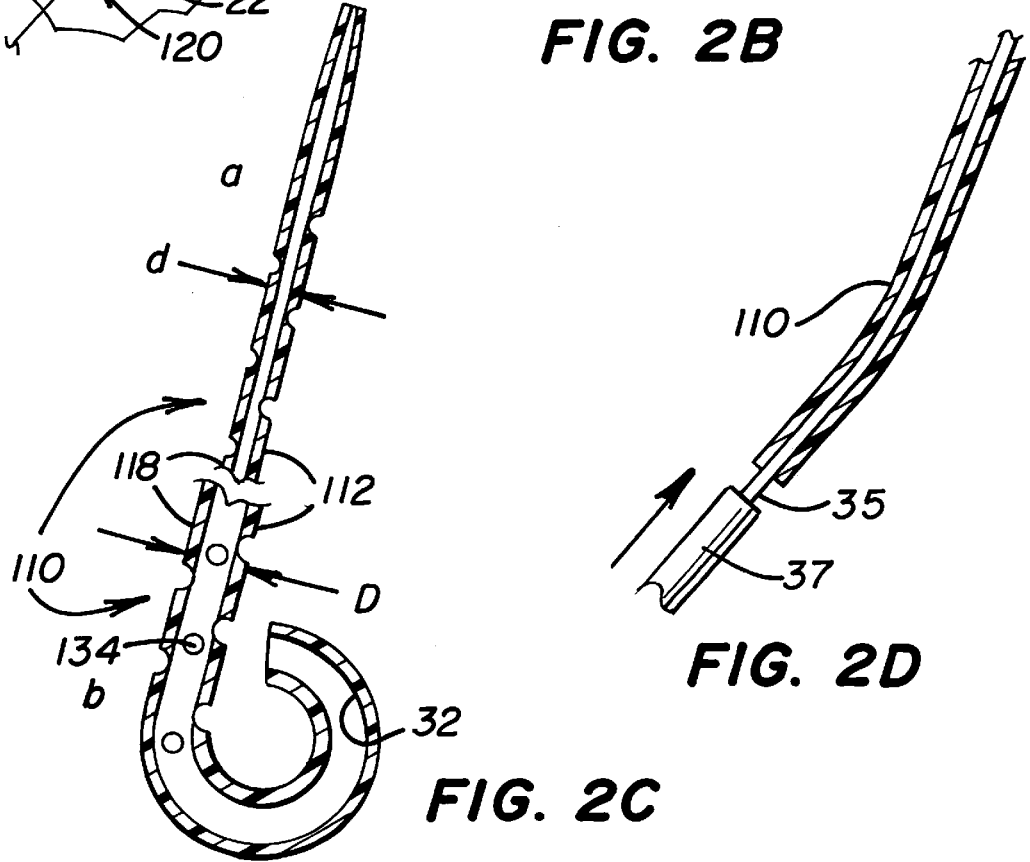

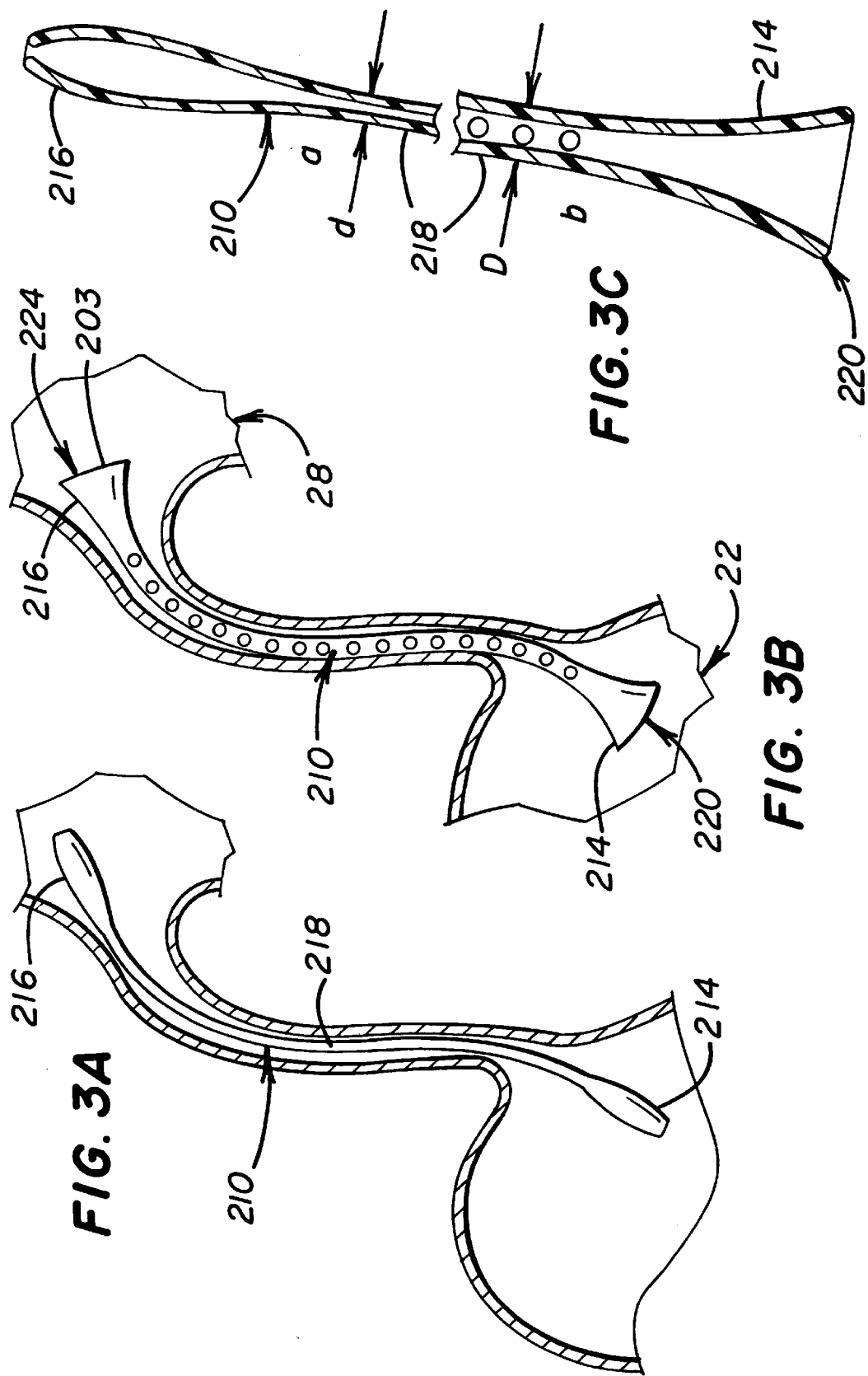

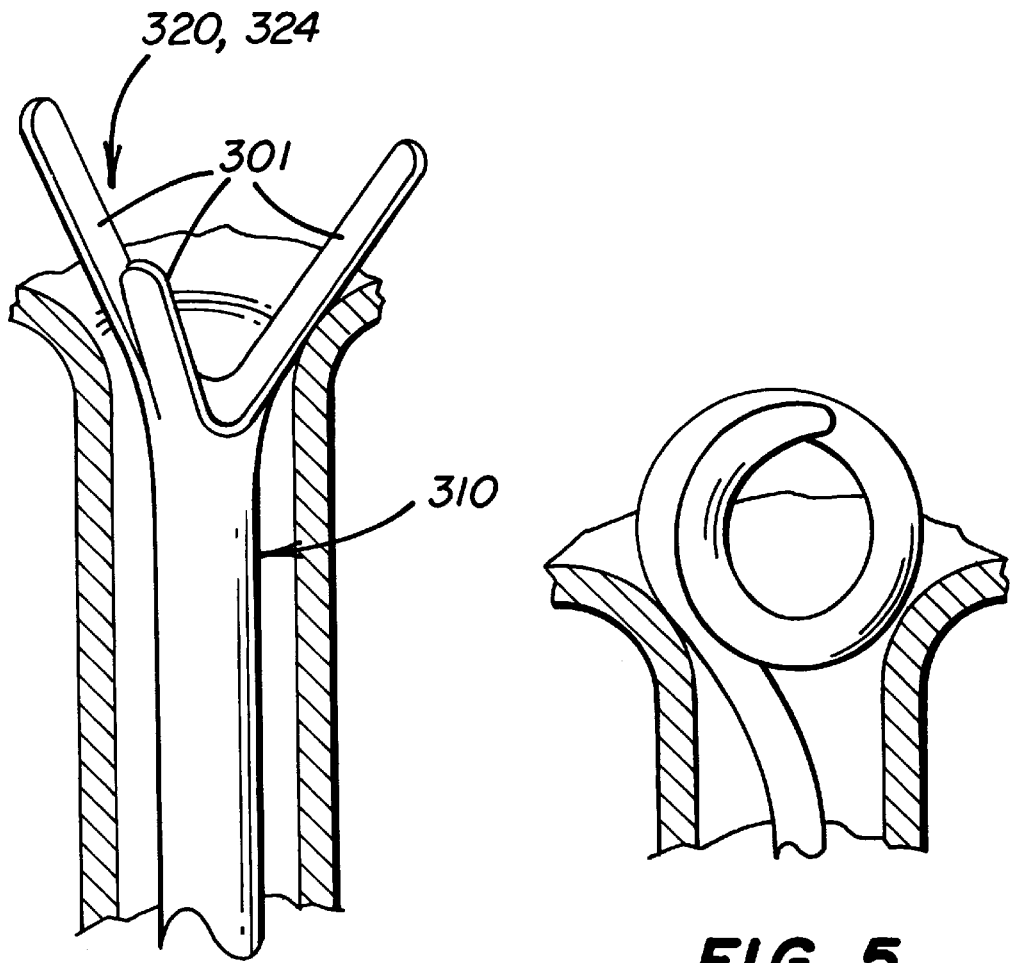
FIG. 4
FIG. 5
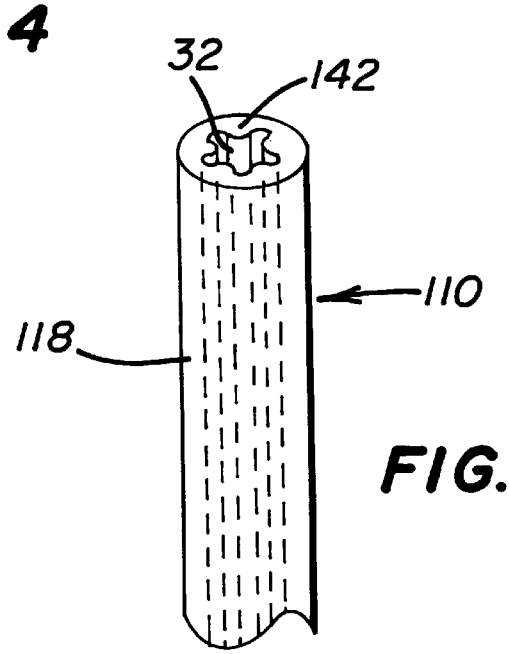
FIG. 10

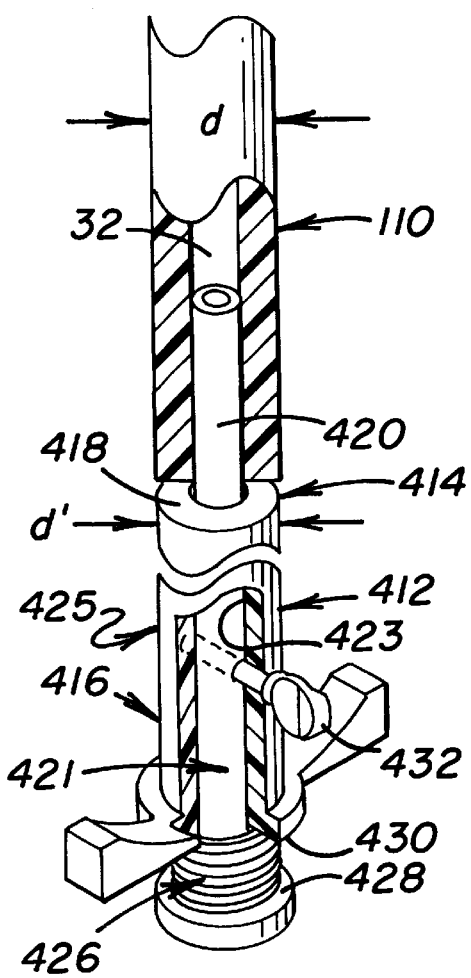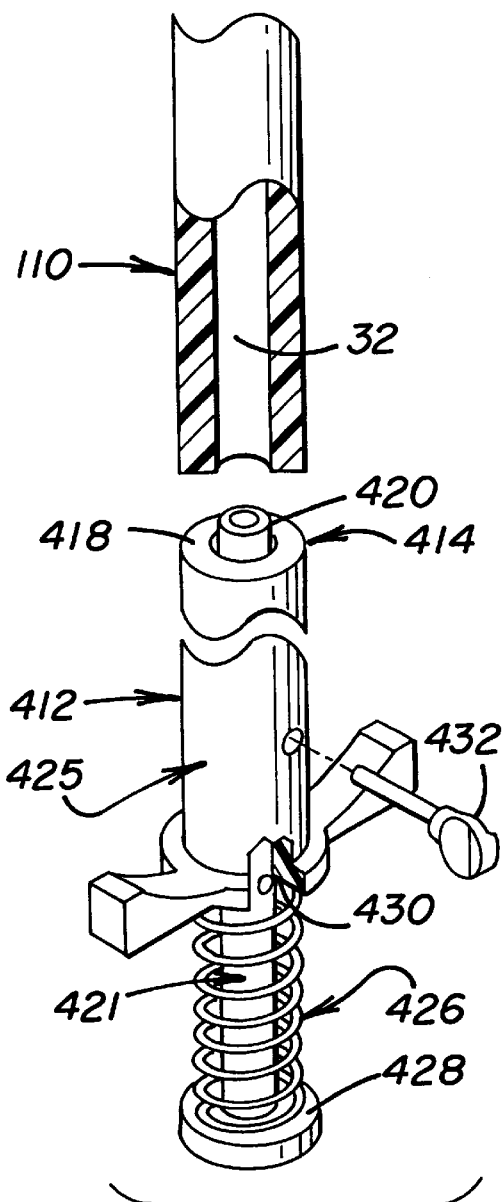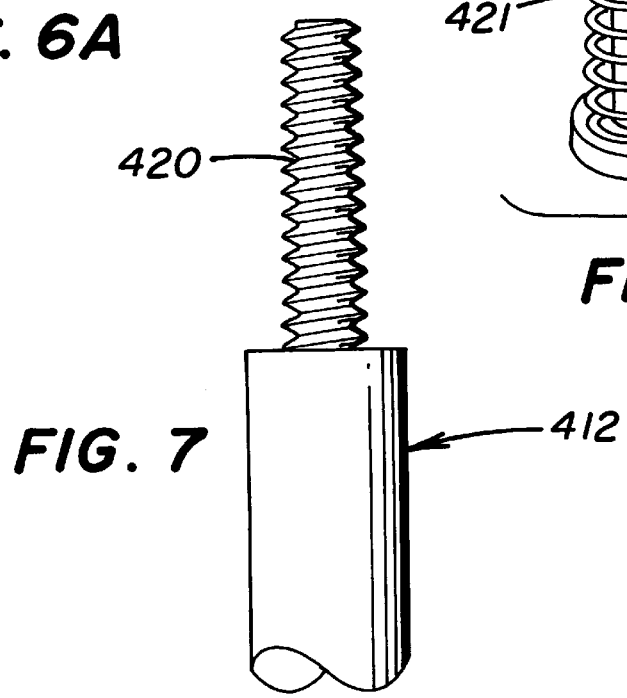
FIG. 6A
FIG. 6B
FIG. 7

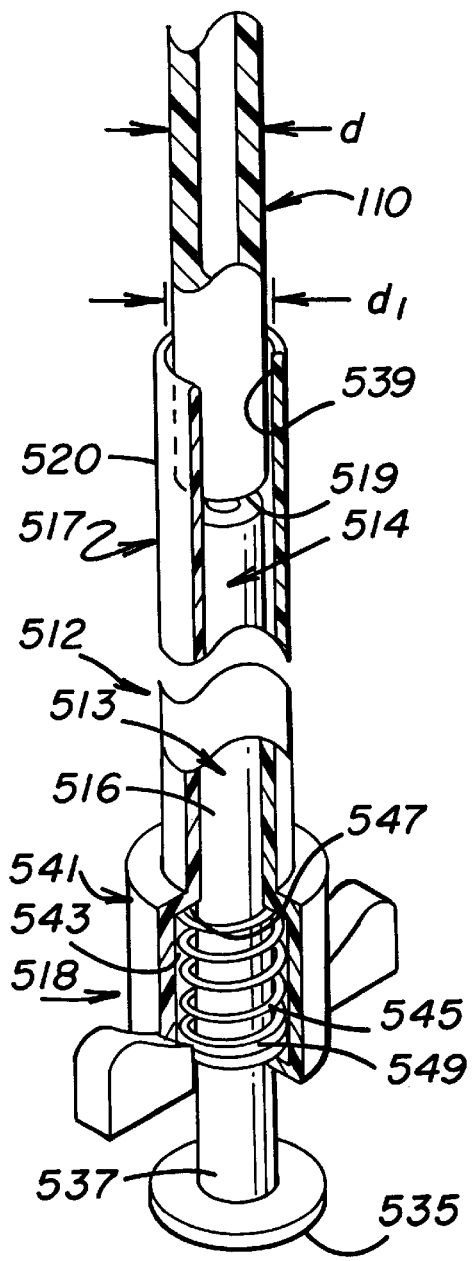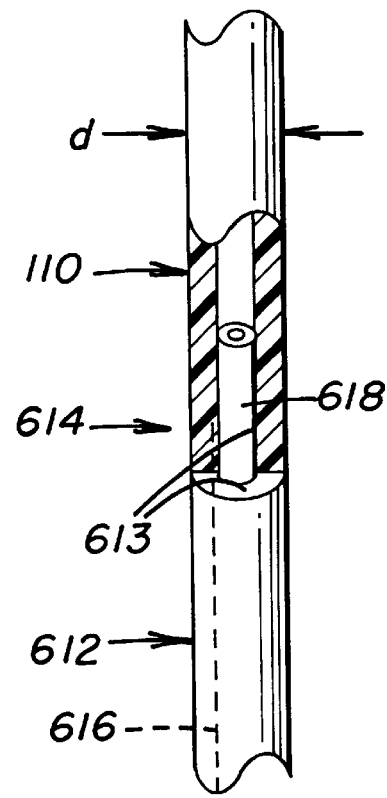
FIG. 8
FIG. 9

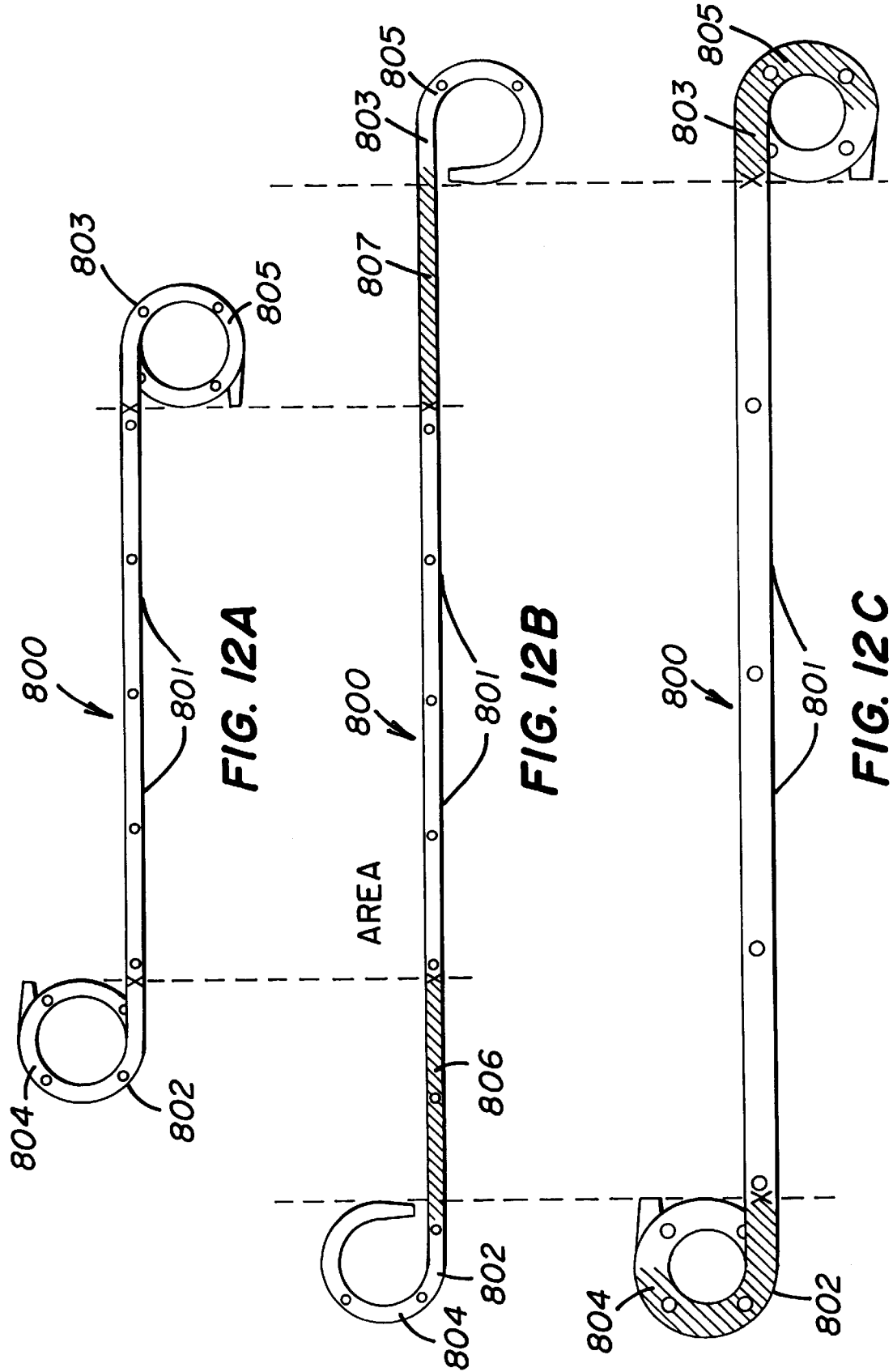

POLYMERIC MEDICAL DEVICE SYSTEMS HAVING SHAPE MEMORY

CROSS-REFERENCE TO RELATED APPLICATION

The present application is a continuation-in-part application of U.S. patent application Ser. No. 08/000,274, filed Jan. 4, 1993, now U.S. Pat. No. 5,599,291, the disclosure of which is hereby incorporated herein by reference in its entirety.

TECHNICAL FIELD

The present invention relates to implantable or insertable medical devices. More specifically, it relates to implantable or insertable medical devices comprising a physiologically acceptable polymer which upon hydration, a change in temperature, and/or a combination thereof, is capable of expanding and softening or to change shape to a predetermined degree and in a predetermined manner, for example, upon implantation in or insertion into a patient. In certain embodiments, for example, stents can be conformed into a first configuration for easy insertion and following insertion can revert into a second configuration for better retention.

BACKGROUND OF THE INVENTION

Stents are used in a variety of medical procedures. For example, stents are often used in connection with assisting drainage from the kidney through the ureter, from the liver through the biliary ducts, from the gall bladder through the cystic, hepatic, or common bile ducts, dorsal or ventral pancreas through the pancreatic ducts, and the like. A leading reason for stent deployment in ducts is to provide drainage to circumvent a blockage. Blockage of ducts in the body can be a serious and very painful affliction that can result in death if not promptly and effectively treated. Blockages can occur for a number of reasons. For example, in the kidney and gall bladder, stones, or debris from such stones, can pass into the ureter or the bile ducts where they become entrapped. Alternatively, cysts or tumors growing against the outer wall of the ducts can cause constriction of the ducts. Similarly, internal or duct wall cysts or tumors can act to block ducts.

In many cases, the problem is solved by surgery, medication, or waiting until debris is naturally cleared from the duct. However, a stent must often be inserted in the duct on at least a temporary basis to provide drainage until the condition can be corrected.

Similarly, blood vessel stents are often used in grafting and supporting blood vessel tissues following invasive medical procedures, such as vascular surgery and angioplasty. Similar concerns are also raised in the catheter and intubation arts, in general, which include, without limitation: intravenous catheters, guiding catheters, sheaths, umbilical catheters, trocar catheters, heart catheters including, valvostomy catheters, angioplasty catheters, arthroscopy catheters, and the like), perfusion catheters, suction catheters, oxygen catheters, endoscopy catheters, endotracheal tubes, stomach tubes, feeding tubes, lavage tubes, rectal tubes, urological tubes, irrigation tubes, aneurysm shunts, stenosis dialators, trocars, and inserters.

Looking in particular at ureteral stents by way of example, there are many different stents available. The main function of each of these ureteral stents is to bypass ureteral obstruction and to provide urary drainage from the kidney to the bladder for a period of time which varies but is usually of the order of a few days to several months.

There are several methods of stent placement within the ureter. One method involves passing a guide wire up the ureter into the kidney. Thereafter, a tubular stent is fed and coaxially slid up the guide wire into the ureter using a tubular stent pusher. An alternate method employs placing a tubular stent having a closed or partially tapered shut proximal end over a guide wire. The stent is thereafter advanced up into the ureter by pushing the guide wire against the closed or partially tapered shut end. Another alternate method is to place the tubular stent over the guide wire with the stent pusher over and affixed to the guide wire behind the stent and thereafter to advance the entire assemblage into the ureter. These methods can also be used, with appropriate surgery to provide access, to insert a stent from the kidney downwardly through the ureter to the bladder.

Early ureteral stents were straight. As a result, after placement into the ureter, these straight stents often migrated or were expelled from the ureter as a result of peristaltic action by the ureter. Later ureteral stents, therefore, were usually designed with means of retention on one or both ends of the stent. The retention means is intended to inhibit stent migration either upward into the kidney or downward into the bladder. Retention means that have been employed are in the form of hooks, pigtails, coils, corkscrews, malecots, barbs, mushrooms, or any other practical shape that will serve the purpose.

Ureteral stents also come in many different lengths. The variations in stent length are often necessary to accommodate the different ureter lengths in different size patients. As a result, a stock of different length ureteral stents must often be kept available. To overcome this problem of stocking many different length ureteral stents, some stents have been designed in the form of an expanding coil or corkscrew as disclosed in U.S. Pat. Nos. 4,531,933; 4,643,716; 4,671,795; and 4,813,925, or utilize connectors as disclosed in U.S. Pat. No. 4,790,810.

In addition to varying lengths, ureteral stents are also made with varying diameters, e.g., from 3 French (1 mm) to 16 French (5.28 mm), and typically, 4.5 French (1.5 mm) to 8.5 French (2.8 mm), and varying degrees of hardness. Ureteral stents with smaller diameters are usually easier to insert but may not provide sufficient drainage, whereas stents with larger diameters allow for increasing drainage capacity through the ureter but may be difficult to insert. Stiff ureteral stents are also easier to insert than are softer stents, but once inserted can lead to increased patient discomfort. Softer stents, on the other hand, provide more comfort for the patient but are more difficult to insert due to their softness. Presently, most available stents are either made of silicone as disclosed in U.S. Pat. No. 4,212,304 or of a harder polymer. Silicone may increase patient comfort, but because of the softness of silicone, it is more difficult to guide the stent into the ureter. Once in the ureter, the softness of the silicone increases the likelihood of migration of the stent because rigid retention means are not available.

To balance ease of insertion, better retention and patient comfort, some ureteral stents have been designed combining a stiff material at the kidney end for easier insertion and better retention with a softer material at the bladder end for patient comfort. These dual hardness stents are disclosed in U.S. Pat. Nos. 4,820,262; 4,874,360; and 4,931,037.

It is at times desirable or necessary to provide a stent which is wider at one end, either its proximal end or its distal end, perhaps as much as 16 French in diameter, and narrower at the other end, perhaps 4.5 French to 7 French. In the past, this has usually required insertion from the proximal (kidney) end of the ureter, a relatively difficult procedure.

Swellable ureteral stents utilizing hydrophilic polymers of the nature set forth in U.S. Pat. No. 4,377,010 and elsewhere, generally as coatings on other materials but also alone, have been investigated using piglets (See An Experimental Study of Hydrophilic Plastics for Urological Use, J. W. A. Ramsey, et al, British Journal of Urology, Volume 58, pp 70–74, 1986 and/or Evaluation of Polymeric Materials for Endourologic Devices, H. K. Mardis, Seminars in Interventional Radiology, Volume 4. Number 1, pp 36–45, March 1987) but have not received acceptance in the medical community. Such stents have not been formulated with different softnesses and/or swellabilities at different portions thereof whereby optimal comfort combined with retainability, ease of insertion and the ability to provide stents which will assume specially desired shapes on hydrating have not been available or contemplated.

Similar problems described above in respect of ureteral stents exist in the art of stents in general. Indeed, many of the aforementioned problems are common to a variety of medical devices that are inserted or implanted in a patient.

Certain work has been done in shape memory technology. For example, certain shape memory metals exist, such as Nitinol. Shape memory has been simulated using certain hydrophilic polymers, i.e., in the context of softening and expanding materials. Mardis, supra. Recently, in U.S. Pat. No. 5,234,457 to Anderson, a type of shape memory was used in intravenous stents. There, a metallic mesh stent was compressed and impregnated with a softenible material, such as a gelatin or a resorbable polymer. The stent, upon softening of the softenible material, would expand against the artery or vein.

Thus, although stents and medical devices have been designed to address one or more of the above problems specifically, there are currently no devices incorporating features that can be used to bypass most of the aforementioned disadvantages. It would thus be desirable to have a medical device that provides one or more of the following attributes, easy insertion or implantation, selectable and different degrees of softening and/or swelling on different portions of the stent, a tapered tip that expands to an adequately large size once expanded, strong retention, insertable or implantable into a small space yet can, if desired, assume a different configuration, size, or shape (i.e., such as a significantly larger diameter at the distal and/or the proximal end upon hydration or another retention means), and, at the same time, increases patient comfort.

DISCLOSURE OF INVENTION

The present invention is directed to overcoming one or more of the problems as set forth above.

In accordance with a first aspect of the present invention, there is provided a polymeric medical device designed for internal use in a patient, comprising a polymer structure that would ordinarily assume a first conformation and a hydrophilic polymer coated upon at least a portion of the structure, the hydrophilic polymer being in a second conformation and having sufficient rigidity whereby the polymer structure is held in the second conformation, wherein upon hydration of the hydrophilic polymer the polymer structure assumes the first conformation. In a preferred embodiment, the hydrophilic polymer is selected from the group consisting of poly(ethylene oxide), polyvinyl pyrrolidone, polyvinyl alcohol, poly(ethylene glycol), polyacrylamide, poly (hydroxy alkyl methacrylates), poly(hydroxy ethyl methacrylate), hydrophilic polyurethanes, HYPAN, oriented HYPAN, poly(hydroxy ethyl acrylate), hydroxy ethyl cellulose, hydroxy propyl cellulose, methoxylated pectin gels, agar, starches, modified starches, alginates, hydroxy ethyl carbohydrates and mixtures and copolymers thereof. In another preferred embodiment, the hydrophilic polymer, upon hydration, softens and expands by from about 5% to about 300%. In another preferred embodiment, the polymer structure comprises an interpenetrating network.

In accordance with a second aspect of the present invention, there is provided a polymeric medical device designed for internal use in a patient, comprising a polymer structure, the polymer structure comprising a first polymer material preconfigured into a first conformation and a second hydrophilic polymer material preconfigured into a second conformation, the first and second polymers having respective mechanical strengths, the mechanical strength of the second polymer material exceeding that of the first polymer material sufficiently so that the polymer structure is in the second conformation, wherein the second polymer material is adapted to lose its mechanical strength upon the occurrence of a triggering event and upon loss of the mechanical strength of the second polymer, the device assumes the first conformation.

In a preferred embodiment, the hydrophilic polymer is selected from the group consisting of poly(ethylene oxide), polyvinyl pyrrolidone, polyvinyl alcohol, poly(ethylene glycol), polyacrylamide, poly (hydroxy alkyl methacrylates), poly(hydroxy ethyl methacrylate), hydrophilic polyurethanes, HYPAN, oriented HYPAN, poly(hydroxy ethyl acrylate), hydroxy ethyl cellulose, hydroxy propyl cellulose, methoxylated pectin gels, agar, starches, modified starches, alginates, hydroxy ethyl carbohydrates and mixtures and copolymers thereof. In another preferred embodiment, the triggering event is an increase in temperature. Or, alternatively, the triggering event is hydration of the second polymer material. In another preferred embodiment, the hydrophilic polymer, upon hydration, softens and expands by from about 5% to about 300%. In another preferred embodiment, the first polymer comprises an interpenetrating network. In still another preferred embodiment, the polymer structure comprises an interpenetrating network.

In accordance with a third aspect of the present invention, there is provided a method to manufacture a polymeric structure having shape memory properties, comprising: providing a polymeric structure comprising a first polymer formed into a first conformation; applying a hydrophilic polymer to at least a portion of a surface of the polymeric structure; deforming the polymeric structure from the first conformation into a second conformation under conditions designed to permit the polymeric structure to retain a memory of the first conformation; and allowing the hydrophilic polymer to harden and hold the polymeric structure in the second conformation.

In a preferred embodiment, the hydrophilic polymer is selected from the group consisting of poly(ethylene oxide), polyvinyl pyrrolidone, polyvinyl alcohol, poly(ethylene glycol), polyacrylamide, poly (hydroxy alkyl methacrylates), poly(hydroxy ethyl methacrylate), hydrophilic polyurethanes, HYPAN, oriented HYPAN, poly(hydroxy ethyl acrylate), hydroxy ethyl cellulose, hydroxy propyl cellulose, methoxylated pectin gels, agar, starches, modified starches, aginates, hydroxy ethyl carbohydrates and mixtures and copolymers thereof. In another preferred embodiment, the hydrophilic polymer, upon hydration, softens and expands by from about 5% to about 300%.

In accordance with a fourth aspect of the present invention, there is provided a method to manufacture a polymeric structure having shape memory properties, comprising: providing a polymeric structure comprising a first polymer and a second polymer formed into a first conformation, the first and second polymers having respective mechanical strengths, the second polymer being capable of losing its mechanical strength upon the occurrence of a triggering event; and deforming the polymeric structure from the first conformation into a second conformation under conditions designed to permit the polymeric structure to retain the memory of the first conformation and to permit the mechanical strength of the second polymer to hold the polymeric structure in the second conformation.

In a preferred embodiment, the second polymer is a hydrophilic polymer. Preferably, the hydrophilic polymer is selected from the group consisting of poly(ethylene oxide), polyvinyl pyrrolidone, polyvinyl alcohol, poly(ethylene glycol), polyacrylmide, poly (hydroxy alkyl methacrylates), poly(hydroxy ethyl methacrylate), hydrophilic polyurethanes, HYPAN, oriented HYPAN, poly(hydroxy ethyl acrylate), hydroxy ethyl cellulose, hydroxy propyl cellulose, methoxylated pectin gels, agar, starches, modified starches, alginates, hydroxy ethyl carbohydrates and mixtures and copolymers thereof. In another preferred embodiment, the triggering event is an increase in temperature. Or, alternatively, the triggering event is hydration of the second polymer material. In another preferred embodiment, the hydrophilic polymer, upon hydration, softens and expands by from about 5% to about 300%.

In accordance with a fifth aspect of the present invention, there is provided a medical device designed for internal use in a patient, comprising a structure that would ordinarily assume a first conformation and a hydrophilic polymer coated upon at least a portion of the structure, the hydrophilic polymer being in a second conformation and having sufficient rigidity whereby the structure is held in the second conformation, wherein upon hydration of the hydrophilic polymer the structure assumes the first conformation. In a preferred embodiment, the hydrophilic polymer is selected from the group consisting of poly(ethylene oxide), polyvinyl pyrrolidone, polyvinyl alcohol, poly(ethylene glycol), polyacrylamide, poly (hydroxy alkyl methacrylates), poly (hydroxy ethyl methacrylate), hydrophilic polyurethanes, HYPAN, oriented HYPAN, poly(hydroxy ethyl acrylate), hydroxy ethyl cellulose, hydroxy propyl cellulose, methoxylated pectin gels, agar, starches, modified starches, alginates, hydroxy ethyl carbohydrates and mixtures and copolymers thereof. In another preferred embodiment, the hydrophilic polymer, upon hydration, softens and expands by from about 5% to about 300%.

In accordance with a sixth aspect of the present invention, there is provided a medical device designed for internal use in a patient, comprising a structure, the structure comprising a first material preconfigured into a first conformation and a hydrophilic polymer material preconfigured into a second conformation, the first material and the hydrophilic polymer having respective mechanical strengths, the mechanical strength of the hydrophilic polymer material exceeding that of the first material sufficiently so that the structure is in the second conformation, wherein the hydrophilic polymer material is adapted to lose its mechanical strength upon the occurrence of a triggering event and upon loss of the mechanical strength of the hydrophilic polymer, the device assumes the first conformation.

In a preferred embodiment, the hydrophilic polymer is selected from the group consisting of poly(ethylene oxide), polyvinyl pyrrolidone, polyvinyl alcohol, poly(ethylene glycol), polyacrylamide, poly (hydroxy alkyl methacrylates), poly(hydroxy ethyl methacrylate), hydrophilic polyurethanes, HYPAN, oriented HYPAN, poly (hydroxy ethyl acrylate), hydroxy ethyl cellulose, hydroxy propyl cellulose, methoxylated pectin gels, agar, starches, modified starches, alginates, hydroxy ethyl carbohydrates and mixtures and copolymers thereof. In another preferred embodiment, the triggering event is an increase in temperature. Or, alternatively, the triggering event is hydration of the hydrophilic polymer material. In another preferred embodiment, the hydrophilic polymer, upon hydration, softens and expands by from about 5% to about 300%.

In accordance with a seventh aspect of the present invention, there is provided a method to manufacture a medical device having shape memory properties, comprising: providing a medical device comprising a first material formed into a first conformation; applying a hydrophilic polymer to at least a portion of a surface of the device; deforming the device from the first conformation into a second conformation under conditions designed to permit the device to retain a memory of the first conformation; and allowing the hydrophilic polymer to harden and hold the device in the second conformation.

Preferably, the hydrophilic polymer is selected from the group consisting of poly(ethylene oxide), polyvinyl pyrrolidone, polyvinyl alcohol, poly(ethylene glycol), polyacrylamide, poly (hydroxy alkyl methacrylates), poly (hydroxy ethyl methacrylate), hydrophilic polyurethanes, HYPAN, oriented HYPAN, poly(hydroxy ethyl acrylate), hydroxy ethyl cellulose, hydroxy propyl cellulose, methoxylated pectin gels, agar, starches, modified starches, alginates, hydroxy ethyl carbohydrates and mixtures and copolymers thereof. In a preferred embodiment, the hydrophilic polymer, upon hydration, softens and expands by from about 5% to about 300%.

In accordance with an eighth aspect of the present invention, there is provided a method to manufacture a medical device having shape memory properties, comprising: providing a medical device comprising a first material and a first polymer formed into a first conformation, the first material and the first polymer having respective mechanical strengths, the first polymer being capable of losing its mechanical strength upon the occurrence of a triggering event; and deforming the device from the first conformation into a second conformation under conditions designed to permit the device to retain the memory of the first conformation and to permit the mechanical strength of the first polymer to hold the device in the second conformation.

In a preferred embodiment, the second polymer is a hydrophilic polymer. In such embodiment, preferably, the hydrophilic polymer is selected from the group consisting of poly(ethylene oxide), polyvinyl pyrrolidone, polyvinyl alcohol, poly(ethylene glycol), polyacrylamide, poly (hydroxy alkyl methacrylates), poly(hydroxy ethyl methacrylate), hydrophilic polyurethanes, HYPAN, oriented HYPAN, poly(hydroxy ethyl acrylate), hydroxy ethyl cellulose, hydroxy propyl cellulose, methoxylated pectin gels, agar, starches, modified starches, alginates, hydroxy ethyl carbohydrates and mixtures and copolymers thereof. In another preferred embodiment, the triggering event is an increase in temperature. In still another preferred embodiment, the triggering event is hydration of the second polymer material. In another preferred embodiment, the hydrophilic polymer, upon hydration, softens and expands by from about 5% to about 300%.

BRIEF DESCRIPTION OF THE DRAWINGS

The invention will be better understood by reference to the figures of the drawings wherein like numbers denote like parts throughout and wherein:

FIG. 12 illustrates a stent manufactured with shape memory with FIG. 12a showing formation of the stent in a first conformation, FIG. 12b showing reconfiguring of the stent into a second conformation with a surface coating of a hydrogel, and FIG. 12c showing reversion of the stent to the first conformation upon hydration.

BEST MODE FOR CARRYING OUT THE INVENTION

Figure 11A:
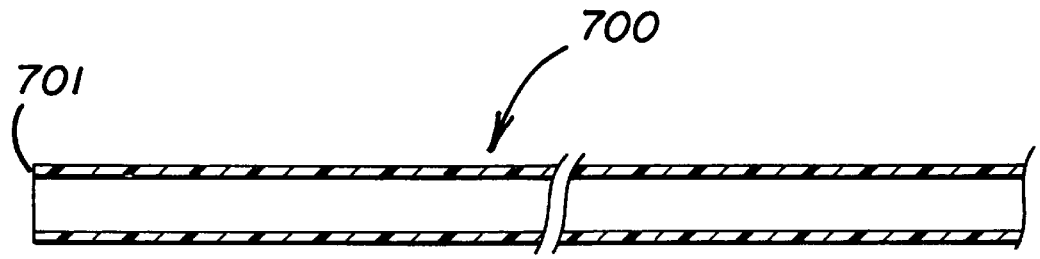
FIG. 11 schematically illustrates a method for introducing shape memory into a medical device, such as a stent.

In accordance with the present invention, there is provided a medical device that is adapted for easy insertion or implantation into a patient but that will change size or shape to assume a configuration different than the configuration prior to insertion or implantation. In general, such ability of the device to change conformation or configuration is made possible by manufacturing a device having a first conformation or configuration and, thereafter, reversibly reconfiguring the device into a second conformation or configuration. In connection with reversibly reconfiguring the device into a second conformation or configuration, the term "reversibly" ordinarily includes making the device capable of assuming the first conformation or configuration upon the occurrence of a triggering event. Events such as temperature changes and hydration or combinations thereof are contemplated. As will be appreciated, what, in essence, is achieved in the present invention is a unique method to control, or provide, "shape memory".

Through the use of shape memory, in general, it is possible to configure a device into a particular, advantageous, configuration. Then, after insertion or implantation into a patient, the device is capable of reverting into a predetermined shape. For example, in the case of stents, it is often desirable to have stents possess end pigtails or enlarged end diameters so that they are not ejected from the duct or do not slide from their place of insertion.

Inclusion of such pigtails or enlarged ends, however, makes insertion of the stents more difficult. While the stent can be mechanically held in a more convenient shape (i.e., straightened out over a guidewire, clamped, or tied), this adds either steps or levels of difficulty to the insertion procedure. Moreover, it is necessary for the physician to take a positive step to release or otherwise remove the mechanical holding.

Accordingly, provision of shape memory in a medical device is preferable. In accordance with the invention, the change from an easy insertion or implantation configuration to the second retention configuration is automatic; it is triggered by the body. In accordance with the invention the trigger can be accomplished by either temperature or hydration (i.e., bodily fluid activation) or a combination thereof. In preferred embodiments, the trigger is accomplished by bodily fluid contact. Moreover, where the trigger is accomplished by contact with a bodily fluid, the effect can be accentuated by temperature change.

Identical concerns that are mentioned above with respect to stents are also applicable in the catheter and intubation arts, which include, without limitation: intravenous catheters, guiding catheters, sheaths, umbilical catheters, trocar catheters, heart catheters including, valvostomy catheters, angioplasty catheters, arthroscopy catheters, and the like), perfusion catheters, suction catheters, oxygen catheters, endoscopy catheters, endotracheal tubes, stomach tubes, feeding tubes, ravage tubes, rectal tubes, urological tubes, irrigation tubes, aneurysm shunts, stenosis dialators, trocars, and inserters, generally. Occasionally it is desirable to insert such tubes or catheters in a first configuration or conformation and, after insertion, have them change to a second configuration or conformation. For example, as shown in Fuqua, U.S. Pat. No. 4,710,181, the disclosure of which is incorporated by reference herein, a folded catheter is held within a sheath to maintain a low profile during insertion. Following insertion, the sheath can be removed, which will allow the folded catheter to expand to its full diameter. A similar result can be accomplished through the shape memory techniques of the invention. For example, through the shape memory techniques of the invention, the device can be manufactured to increase in diameter upon insertion. Alternatively, a sheath system can be used where a device is inserted within the sheath and the sheath is designed to lose its mechanical strength and release the interned device.

Similarly, in the case of intraocular lenses, it is often desirable to have the lenses folded for insertion. This has typically been accomplished by clamping the lenses in half. Through use of shape memory technology, lenses can be manufactured in a first open configuration, reconfigured into a second folded configuration, sold in such folded configuration, and, upon insertion into an eye of a patient, win open to the first configuration.

Accordingly, it will be appreciated that the provision of shape memory has broad applicability in the medical device art. In particular, devices that are designed for implantation or insertion in the body are improved in accordance with the invention. Thus, shape memory is an attractive method for overcoming the inconveniences and problems associated with changing a configuration or conformation of a medical device in vivo.

There are several approaches that can be used to achieve shape memory in accordance with the invention. Preferably, for example, reconfiguring the device is accomplished by, in appropriate cases, heating the device and manipulating the device to a second conformation or configuration. Alternatively, reconfiguring in another preferred embodiment is accomplished by manipulating the device to a second configuration or conformation and applying a substance that will cause the second conformation or configuration to be maintained. For example, a hydrogel may be applied to selected portions of a polymeric medical device which will reversibly hold the device in the second conformation or configuration until the device is exposed to water at which time it will revert to the first conformation or configuration.

In a closely analogous embodiment, a device may be manufactured from a composite polymeric matrix including generally hydrophobic and hydrophilic polymers. For example, an interpenetrating matrix of a hydrophilic and a hydrophobic polymer as described in U.S. Pat. Nos. 4,883,699 and 4,911,691, the disclosures of which are hereby incorporated by reference. If appropriately manufactured (i.e., including appropriate ratios of the hydrophobic and hydrophilic polymer mixtures) the device can be manipulated, while hydrated, into a second conformation and allowed to dry while being maintained in a second conformation or configuration. Thereafter, when the device is rehydrated, it will return to the first configuration or conformation. Devices manufactured from an interpenetrating network, for example, can also be fashioned through the use of heating as mentioned above.

These separate embodiments can be viewed in several basic categories of reconfiguring of the device from the first conformation to the second conformation: thermal processing, surface coating, interpenetrating network technologies, and combinations thereof. Each of these technologies will be discussed serially below.

I. Thermal Processing

Referring now to FIGS. 11a through 11e, a stent 700 is provided having a distal end 701. The stent 700 is formed from a composite of polymers having disparate glass transition temperatures. Preferably, one of the polymers has a glass transition temperature at about body temperature referred to herein as the "first polymer" and another of the polymers has a glass transition temperature at a temperature significantly exceeding the glass transition temperature of the first polymer, referred to herein as the "second polymer."

In FIG. 11a, while the stent 700 can be manufactured in any shape, it is pictured in the Figure in a straight configuration. In manufacture, for example, the stent 700 can be melt extruded in a straight configuration or molded into another configuration. The stent 700, or other medical device, can be manufactured as an interpenetrating network of polymers (as described in U.S. Pat. No. 4,488,699, the disclosure of which is hereby incorporated by reference).

Alternatively, the medical device can be manufactured in discreet polymer layers (as described in U.S. Pat. Nos. 4,627,844, 4,636,346, 4,846,812, and 4,994,047, the disclosures of which are hereby incorporated by reference).

Figure 11B:
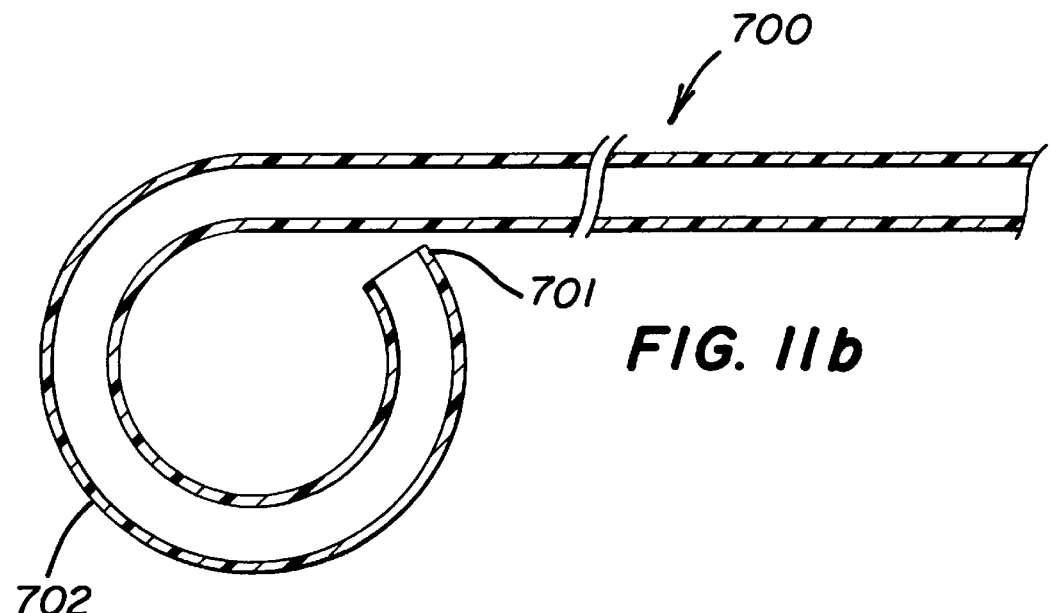

Referring now to FIG. 11b, the stent 700 is heated to a temperature above the glass transition temperature of the second polymer and shaped into an appropriate shape. In the illustrated embodiment, a partial pigtail 702 is formed in the distal end 701 of the stent 700. Shaping can be accomplished using appropriate mandrels and/or shaping tools which are well known to those of skill in the art. This configuration is referred to as the first configuration. Generally, the stent is cooled to a temperature below the glass transition temperature of the first polymer after being configured in the first configuration while it is maintained in the first configuration. As will be appreciated, the stent may be cooled to a temperature below the first or second polymer. The primary purposes of the cooling step are to enable the ease of handling of the device and also to provide memory to the device of the first conformation.

Figure 11C:
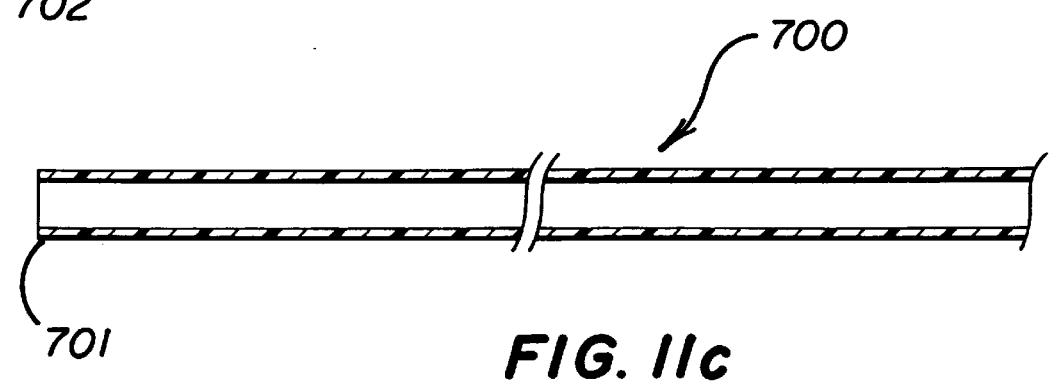

Thereafter, in FIG. 11c, the stent 700 can be heated to a temperature exceeding the glass transition temperature of the first polymer and shaped into a second configuration. Necessarily, the polymers are selected so that the glass transition temperature of the first polymer is lower than the forming temperature of the second polymer. In this way, the "memory" of the first configuration is retained by the polymer. Then, the stent 700, or other medical device, formed into the second configuration, is cooled below the first polymer glass transition temperature while it is maintained in such configuration.

Figure 11D:
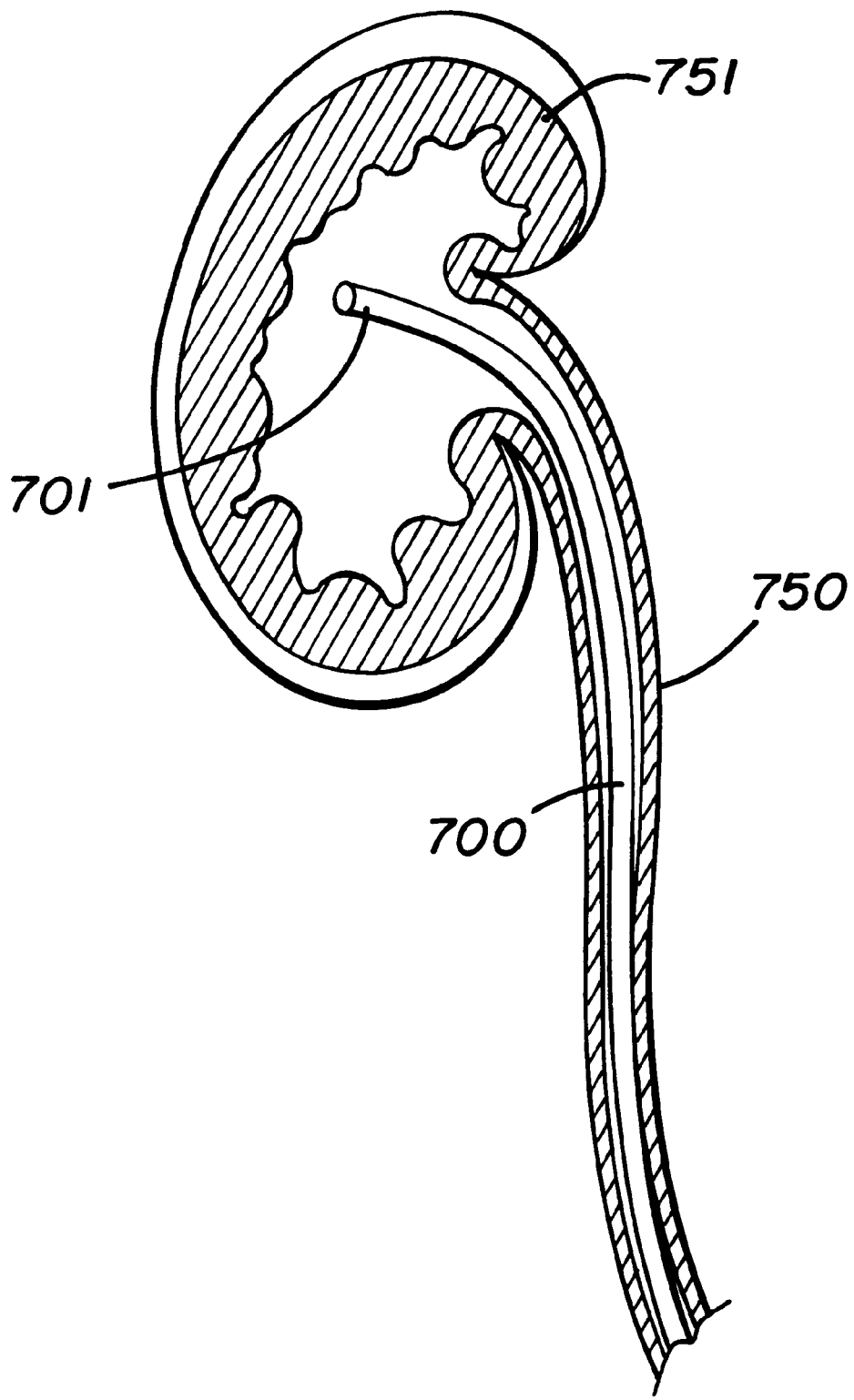
Figure 11E:
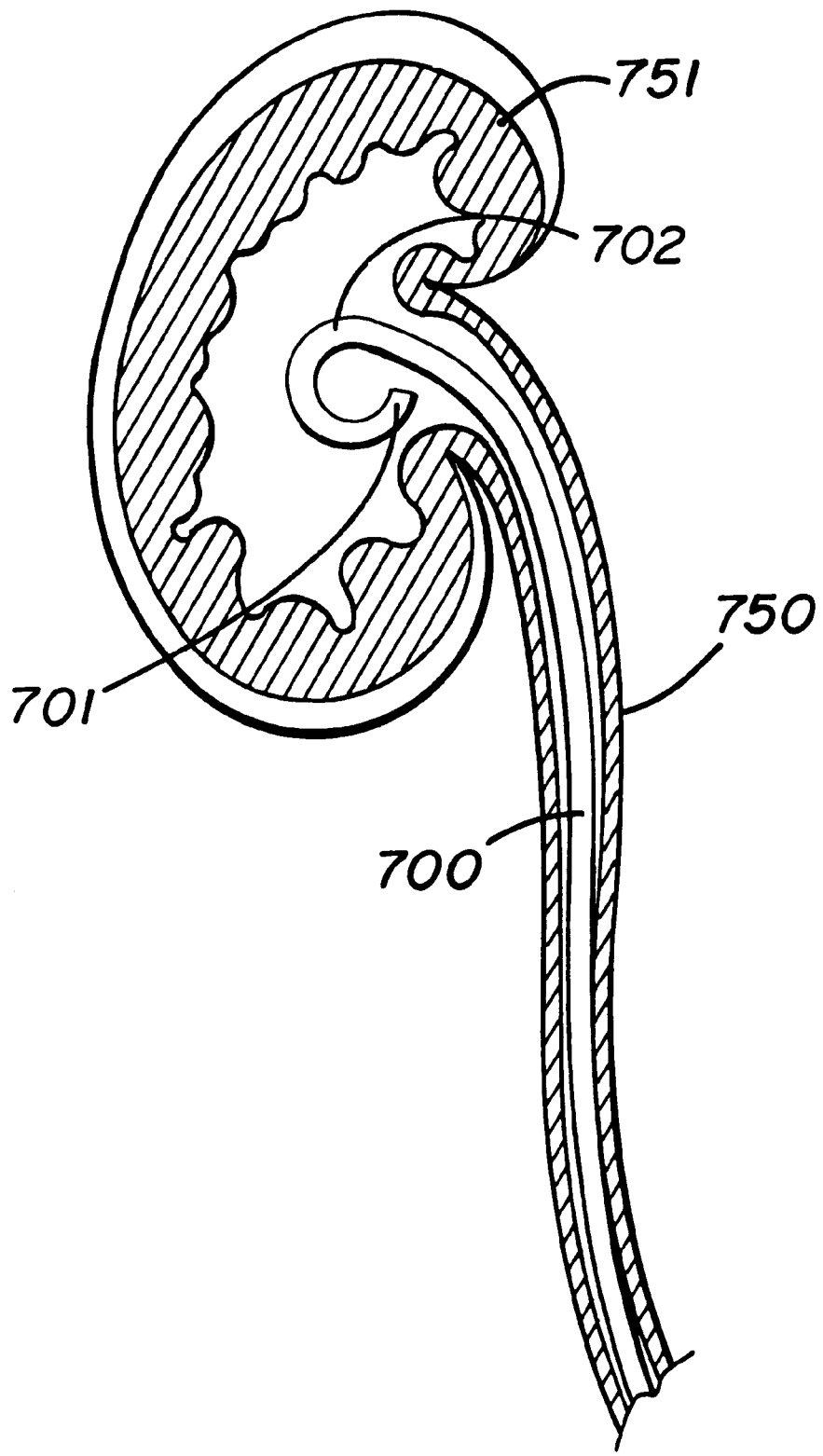

As illustrated in FIG. 11d, the stent 700 formed into the second configuration is then easily inserted into the body, herein pictured during insertion into through the ureter 750 and into the kidney 751 of a patient. Insertion is accomplished in any conventional manner, such as insertion through the urethra (not shown) and traversing through the bladder (not shown) using a guidewire or other insertion device. As shown in FIG. 11e, Upon insertion as described, the stent 701 will heat to a temperature approaching or exceeding the glass transition temperature of the first polymer. At such temperature, the mechanical strength of the first polymer will become insufficient to hold the second configuration and the stent 700 will revert to the first configuration. Such shape is the shape dictated by the shape which it was given in FIG. 11b (i.e., the first configuration). As will be appreciated, the shape in FIG. 11b was dictated by the glass transition temperature of the second polymer which allowed configuring of the device into the first configuration.

Methods to manufacture medical devices from composite polymers with appropriate glass transition temperature characteristics are well known to those of ordinary skill in the art. As well, appropriate polymers to meet the shape memory objectives of the invention will be readily selectable by those of skill in the art without undue experimentation.

A limitation of medical devices manufactured through the thermal processing techniques described above, is that during shipping, storage, insertion, implantation, and the like, it is expected that the glass transition temperature of the second polymer may be prematurely attained and the device will revert from the second configuration to the first configuration before it is desirable. While, in many situations, it may be possible to clamp or otherwise package devices so that the problem is minimized, it would be preferable to avoid the problem more completely.

Accordingly, the following embodiments are provided where effects of elevated temperatures will be less deleterious to maintenance of the second conformation or configuration.

II. Surface Coating

In accordance with another embodiment of the invention, bodily fluid softenible polymers or other coatings can be used to hold a device in a second configuration or conformation after manufacture in a first configuration. This technique closely follows the illustrations provided in FIGS. 11a through 11e with reference to a stent 700.

As described in connection with FIG. 11 (relating to thermal processing), the medical device is first configured into a desired first configuration or conformation. In a preferred embodiment, this is accomplished in FIGS. 11a and 11b, where the stent 700 is formed into a desired shape. As will be appreciated, the stent can be formed in one configuration (i.e., straight (FIG. 11a)) and thereafter shaped into the first configuration (FIG. 11b). Or, the desired first configuration can be formed in a single step.

In FIG. 11c, the stent 700 is formed into the second configuration. To accomplish this change in conformation or configuration, the stent 700 in FIG. 11b is surface coated with a material, referred to herein as the softenible material, that has sufficient mechanical strength to hold the device in a second configuration that will soften, erode, or dissolve away (generally, lose its mechanical strength) upon exposure to a bodily fluid (i.e., hydrated), upon attaig a temperature near body temperature, or a combination. Following surface coating of the stent 700 with the softenible material, the stent 700 is manipulated into the second conformation and the coating is allowed to harden which will hold the stent 700 in the second configuration.

In a preferred embodiment, the softenible material is a polymer that is generally hydrophilic, such as poly(ethylene oxide), polyvinyl pyrrolidone, polyvinyl alcohol, poly (ethylene glycol), polyacrylamide, poly(hydroxy ethyl acrylate), poly (hydroxy alkyl methacrylate) (such as poly (hydroxy ethyl methacrylate) (poly(HEMA))), hydrophilic polyurethanes, HYPAN and oriented HYPAN (block copolymers of polyvinylalcohol and polyacrylonitrile, made by selectively hydrolyzing blocks of the polyacrylonitrile), HEPU (hydrophilic polyurethane block copolymers with polyethylene oxide), hydroxy ethyl cellulose, hydroxy propyl cellulose, methoxylated pectin gels, agar, a starch such as cornstarch, a modified starch, an alginate, a hydroxy ethyl carbohydrate, or the like. In highly preferred embodiments, the softenible material is a hydrogel, such as polyethyleneoxide available from Union Carbide, or polyvinylpyrrolidone, available from BASF.

Thereafter, as shown in FIGS. 11d and 11e, when the stent 700 is inserted into the body, the softenible surface coating will lose its mechanical strength and the stent 700 will return to the first configuration.

In this embodiment, the medical device is typically formed of a polymer material. Generally, any biocompatible polymer will be acceptable. When implantation or relatively long indwelling time periods are required of the medical device, generally highly biocompatible polymers are used.

Surface coating can be accomplished through a variety of processes that are well known to those of ordinary skill in the art. For example, surface coating may be accomplished by dipping, spraying coextruding, laminating, and/or injection molding the coating onto a substrate polymer. Moreover, surface coating can be accomplished on either an "internal" or an "external" surface of the device. For example, in the case of a stent a catheter, a surface coating may be applied to the external surface of the article or it may be applied inside of the lumen with equal success. One advantage of external surface coating is ease of application. However, the ease of application will, in certain situations, be outweighed by an advantage of internal coating which includes the ability to maintain a lower profile of the device. When the surface coating is internal to the device, the coating will soften, expand, dissolve away, or otherwise loose mechanical strength and allow the device to revert to the first conformation or configuration. Where the surface coating does not dissolve away or otherwise open the lumen, the lumen will need to be made of a large enough diameter to be efficacious for the intended purpose.

Nevertheless, a limitation of simple surface coating comes when the softenible surface coating simply dissolves away from the device. If the softenible coating is designed to dissolve away, the material forming the coating will be introduced into the patient's body. Therefore, the material must be highly biocompatible in order to avoid causing deleterious effects in a patient's body. Examples of preferred materials include polyvinlypyrrolidone, polyethylene oxide, poly(HEMA), polyvinylalcohol, starches, alginates and cellulose. Alternatively, the surface coated device can be cross-linked to limit or prevent solvation of the coating. As will be appreciated, through appropriate amounts cross-linking, the coating will be less soluble in bodily fluids but will still undergo softening, expansion, or loss of mechanical strength to achieve the intended result. The amount of cross-linking necessary for a given application can be readily determined by those of ordinary skill in the art by routine experimentation.

III. Interpenetrating Network Technology

In a closely analogous manner to that discussed for surface coating, above, an interpenetrating network of a hydrophobic and a hydrophilic polymer can be formed. However, in this embodiment, there is no step of surface coating. Rather, the device is manufactured as a composite of materials: one that is relatively hydrophiic and another that is relatively hydrophobic or non-hydrophilic. There are several methods that can be used for the manufacture of medical devices formed with interpenetrating networks that will have shape memory.

For example, in manufacture, the device may be hydrated (i.e., exposed to a fluid resembling a bodily fluid or water) and shaped into a second conformation or configuration. Thereafter, the device is allowed to harden in a second conformation. Then, upon insertion or implantation into the patient, the device will become hydrated and return to the first configuration.

Alternatively, the device can be manufactured using the techniques described above for thermal processing. However, rather than using temperature (primarily) as the trigger for causing a change in conformation from the second configuration to the first configuration, swelling or loss of mechanical strength of the hydrophilic polymer in the interpenetrating network is utililed.

The process of manufacture, in either case, closely follows the procedure discussed in connection with FIG. 11.

Medical devices formed from interpenetrating networks that are given shape memory properties are highly desirable since none of the polymers are washed away and diffused throughout the body of a patient. Instead, the hydrophilic polymer is a part of the polymer matrix of the device and is retained as part of the structure of the device. The hydrophilic polymer, which in its nonhydrated state, acts to hold the device in the second conformation, simply loses its mechanical strength and allows the shape dictated by the hydrophobic or non-hydrophilic polymer to be assumed, i.e., the first conformation.

IV. Discussion of Material Technology

As was mentioned above, the invention has broad applicability to the medical device field. Certain preferred embodiments are described below, particularly relating to the stent art and more particularly relating to uretal stents. However, as will be appreciated to those of ordinary skil in the art, such embodiments are illustrative rather than limiting.

The hydrophilic component is suitably a polymer that absorbs at least about thirty percent (30%) water, preferably at least about fifty percent (50%) water, more preferably about one hundred percent (100%) water or more, e.g., one hundred fifty percent (150%) water, by weight based on the weight of the hydrophilic polymer. The hydrophilic polymer, preferably, is capable of forming a hydrogel upon absorption of water.

The hydrophilic polymer can suitably be selected from the group consisting of poly(ethylene oxide), polyvinyl pyrrolidone, polyvinyl alcohol, poly(ethylene glycol), polyacrylamide, poly(hydroxy ethyl acrylate), poly(hydroxy ethyl methacrylate), hydroxy ethyl cellulose, hydroxy propyl cellulose, methoxylated pectin gels, agar, a starch such as cornstarch, a modified starch, an alginate, a hydroxy ethyl carbohydrate, or the like. Copolymers of the monomers forming such polymers are also suitable. Mixtures of any of the above are likewise suitable. The polymer should preferably allow the device to swell to a selected percent after hydration.

The degree of swelling of the hydrophilic component, and consequently, the device, can also be controlled or tailored as desired by controlling the amount of cross-linking of the polymer. The amount of cross-lining can be adjusted, as is well known in the art, chemically and/or by adjusting the amount of radiation applied to cause the cross-linking. The higher the degree of cross-linking, the less will be the swellability of the hydrated polymer and thus of the particular device.

The device preferably comprises a hydrophilic component and a non-hydrophilic component in a selected ratio. The ratio of hydrophilic component to non-hydrophilic component is preferably adjustable so as to allow the polymer to expand the initial cross ureteral stent outer diameter d to a desired extent, for example, by from about five percent (5%) up to about three hundred percent (300%), or more preferably from about fifteen percent (15%) up to about fifty percent (50%), upon hydration.

The polymer can be formulated so that upon hydration one portion of a device, the device softens to a greater degree than does another portion of the device. To achieve this dual hardness after hydration, initially the device can be processed differently at different positions of the device. For example, one portion of the device can be cross-linked more than is another portion of the device, e.g., by exposing it to more polymerization initiating radiation. This can be accomplished through shielding or other conventional methods, such as bonding dissimilar components which is often referred to as butt joining.

While devices in accordance with the invention can be formulated of a polymer which comprises only a hydrophilic component, preferably the device will also comprise a non-hydrophilic component. The non-hydrophilic component comprises a polymer which does not substantially absorb or attract water. Preferably, the non-hydrophilic polymeric component is capable of absorbing water in an amount of no more than about thirty percent (30%), more preferably no more than about fifteen percent (15%) and still more preferably no more than about ten percent (10%), by weight, based on the weight of the non-hydrophilic polymeric component.

The non-hydrophilic component can be, for example, a thermosetting elastomer such as silicone, a polyurethane such as an aliphatic or aromatic polyurethane, a polyether polyurethane, a polyester polyurethane, and a polycarbonate polyurethane; an ethylene copolymer such as ethylene-vinyl acetate copolymer; a polyamide, in particular a polyamide of low crystallity; an aliphatic polyester or mixtures or copolymers thereof. In addition, the nonhydrophilic component may include a metal and, in particular, certain shape memory metals, such as Nitinol, tungsten, tantalum, and other similar metals. The nonhydrophilic component, as win be appreciated can be provided in solid or other form, such as in a mesh.

Examples of swelling (and softening) polymers having both hydrophilic and non-hydrophilic components and which are useful in the practice of the invention are those described in, for example, U.S. Pat. No. 4,883,699, issued Nov. 28, 1989 which is incorporated herein by reference.

This patent discloses a suitable composition for the polymer which comprises:

(a) a first phase which comprises a substantially non-hydrophilic polymeric component; and (b) a second phase which comprises a hydrophilic polymeric component; said material (i) being capable of absorbing water to an extent that it swells with a swelling ratio of at least about 1.3:1, preferably from about 1.5:1 to 3.5:1 (and generally softens with a softening ratio of at least about 2:1)

Also useful are those swelling and softening hydrophilic polymers described in U.S. Pat. Nos. 4,359,558; 4,424,305; 4,454,309 and 4,439,583 of Tynsdale Plains-Hunter Ltd. incorporated herein by reference. The preferred polymer composition of these patents essentially comprises a polyurethane diacrylate composition having from about ninety (90) to about sixty five (65) weight percent of a hydrophilic polyurethane resin and from about ten (10) to about thirty five (35) weight percent of a diacrylate.

Still another polymer which is suitable is the thermoplastic elastomeric hydrophilic polyurethane described in U.S. Pat. No. 5,061,254 of Becton-Dickenson and Company which is incorporated herein by reference.

In accordance with one embodiment of the invention, the device can be formulated of a physiologically acceptable polymer that is capable of softening and expanding to a predetermined degree upon hydration then subsequently shrinking to a desired extent, for example, to roughly its non-hydrated size, to allow it to be readily withdrawn from the patient after a desired length of time. To accomplish this, the polymer can comprise a soluble hydrophilic component and a non-soluble non-hydrophilic component having softening and expansion characteristics as previously described. The hydrophilic component and non-hydrophilic component can be selected from the respective groups indicated above. As the hydrophilic component dissolves or degrades the device will then shrink.

As another alternative, the device can be formulated of a central cylindrical core of a physiologically acceptable polymer that is capable of softening and expanding to a predetermined degree upon hydration but that will not dissolve or biodegrade readily in the ureter or in another selected duct or bodily cavity. The device can further include an outer layer formulated of a physiologically acceptable polymer that is readily soluble or biodegradable in the ureter. For example, the outer layer can be a substantially non-cross-linked hydrophilic polymer. The dissolving of all or part of the outer layer then leads to a subsequent-to-insertion shrinking of the device to a desired extent, for example, to roughly its non-hydrated size, to allow it to be readily withdrawn from the patient after a desired length of time.

The expansion and softening of a non-hydrated device normally occurs from within forty five (45) minutes to a few hours after its insertion into the body of a patient. The subsequent shrinking of the device to its non-hydrated size or smaller usually takes from three days to three months as the soluble (or degradable—the term soluble is used herein to encompass al means by which the device shrinks) component is dissolved or degraded from the device. The rate of shrinking and the final shrink size can be controlled by the volume ratio of hydrophilic component to non-hydrophilic component and/or the extent to which the hydrophilic component is cross-linked. The higher the initial volume of soluble component, the smaller the size of the device after the soluble component has dissolved. In addition, the higher the degree to which the soluble component is cross-linked, the slower the rate at which the soluble component will dissolve and thus the slower the rate at which the device will shrink.

The shape and/or expansion of a device can also be controlled by beginning with a non-hydrated device with substantially a constant outer diameter along its length, heating the non-hydrated device above the forming temperature of the non-hydrophilic component, which is above the melting temperature of the hydrophilic component, while in contact with a first mandril which molds the device to a different configuration, followed by cooling the device below the melting temperature of the hydrophilic component while it is still shaped by the first mandril, removing the device from the first mandril, positioning the device on a second mandril which defines a substantially different shape or configuration, heating the device to a temperature above the melting temperature of the hydrophilic component but below the forming temperature of the non-hydrophilic component, molding the device against the second mandril, and cooling the device to a temperature below the melting temperature of the hydrophilic component while it is still shaped by the second mandril. On later insertion into the body, hydration of the hydrophilic component, which substantially reduces the strength of the shape set by the hydrophilic component, allows the shape molded against the second mandril to be lost and the device will return to the shape molded against the first mandril.

In each of these embodiments, shape memory is introduced into the stent or other device through use of interpenetrating network technology utilizing a thermal-type processing. It will be appreciated that these embodiments could also be manufactured using a surface coating (described above) that would act to hold the stent in its preinsertion conformation and then would dissolve away or soften to allow expansion or formation of the desired shape. Alternatively, the hydrophilic polymer can be hydrated and the device configured into the first conformation and dried in the second configuration. Upon hydration, the device will assume the first conformation, i.e., an enlarged diameter.

Useful biodegradable polymers include polyorthoesters, polylactides, polyglycolides and copolymers, collagen, polycaprolactone and polyglutonates. One suitable biodegradable polymer comprises L(-)lactide, glycolide and epsilon-caprolactone in selected ratios. An example of a biodegradable polymer having L(-)lactide, glycolide and epsilon-caprolactone which is useful in the practice of the invention is described in U.S. Pat. No. 5,085,629 issued Feb. 4, 1992 which is incorporated herein by reference.

Suitable dissolvable polymers include polyethylene oxides, polyvinylacetates, polyvinylpyrrolidone, polyethylene oxide based polyether urethanes, starches and cellulose derivatives such as hydroxyethyl cellulose. The dissolvable polymers are generally preferred since they can be readily formulated so as to dissolve in minutes to hours. The rate at which the polymer hydrates and degrades can be controlled by controlling the molecular weight and the amorphous nature of polymer composition.

Mineralization with agents such as cholesterols, uric acids and cystines, and calcification, particularly with agents such as calcium phosphate, calcium oxalate, struvite, brushite, and calcium apatite, can be inhibited by various chemicals. Such inhibitory chemicals can be incorporated into implants, stents, and devices by the various methods referenced above. Anti-calcification chemicals or additives are known in the art and include certain diphosphonates, especially ethanehydroxy diphosphonate (EHDP), certain metal ions, especially aluminum and iron and alpha amino oleic acid derivatives to name but a few. For example, hydroxyethylidene biphosphonic acid dispersed in polyurethane (PU) articles inhibits calcification of the polymer and of the surrounding tissue and EHDP can diffuse through PU membranes and inhibit calcification of tissue. Aluminum or iron ions and oleic acid compounds have all been reported to reduce calcification of bioprosthetic porcine heart valves. Anticalcification techniques are disclosed in U.S. Pat. No. 4,753, 652, the disclosure of which is hereby incorporated by reference.

It will also be appreciated that a variety of other diagnostic and therapeutic agents can be incorporated into polymers in a manner adapted to allow the agent to be released and allow diagnosis and/or therapy. For example, in the intravenous art there is a great deal of current interest in the prevention of restenosis. Agents designed to prevent restenosis may be capable of delivery through incorporation within the polymers of the present invention. For a review of certain of the current strategies for preventing restenosis, see Epstein et al. *J Am Coll Cardiol* 23(6):1278–88 (1994) the disclosure of which is hereby incorporated by reference. In antitumor applications, there are a huge number of potential chemo- and radiotherapeutic agents available. See Calabresi et al. *Antineoplastic Agents* pp. 1209–63 in "The Pharmacological Basis of Pharmacology" (Goodman et al. 8th ed. Permagon Press (1990)), the disclosure of which is hereby incorporated by reference. Such agents can be incorporated into polymers and can be delivered to a tumor site, such as in ductal tumors. Similarly, antimicrobial agents can be suitably incorporated into and released from polymer structures. Some exemplary antimicrobial agents are described in Sande et al. *Antimicrobial Agents* pp. 1018–1201 and Webster et al. *Chemotherapy of Parasitic Infections* pp. 954–1017, both in "The Pharmacological Basis of Pharmacology", supra.. Hormones, in particular growth hormones, can also be delivered through use of the present invention. Examples of appropriate hormones are described in Murad et al. *Hormones and Hormone Antagonists* pp. 1332–1522 in "The Pharmacological Basis of Pharmacology", supra.

In order to achieve the purposes of the present invention a variety of techniques can be used. In general, as described above, the present invention in one aspect may be summarized as the use of a first material to hold a second material in a defined shape so the material may be inserted or implanted into the body and then upon a triggering event change shape. In a preferred embodiment, a hydrophilic material is used as the first material for the purpose of holding the second material in the defined shape. The triggering event, in such embodiment is an act of hydration of the hydrophilic material which results in a general softening and/or loss of mechanical strength of the hydrophilic polymer. Such softening and/or loss of mechanical strength releases the second material from the defined shape in which it was held by the first material.

EXAMPLES

Example 1

Preparation of a Shape Memory Stent Using Surface Coating

In this example, a surface coating of a hydrophilic polymer is used as a first material to hold a second interpenetrating network material in a predetermined position. In this example, the hydrophilic polymer loses mechanical strength upon exposure to a bodily fluid so that the second material is capable of returning to a shape that it was conformed into prior to coating with the first material.

Referring to FIGS. 12a through 12c, a shape memory uretal stent was prepared using a stent 800 formed from an Aquavene™ interpenetrating network using polyurethane as the non-hydrophilic polymer and polyethyleneoxide, polyvinylpyrrolidone, orpolyvinylalcohol as the hydrophilic polymer as described in U.S. Pat. No. 4,994,047. The stent 800 was melt extruded in a straight configuration. The stent 800 had a connecting section 801 and end sections 802 and 803. Pigtails 804 and 805 (540°) were formed on each of the end sections 802 and 803 of the stent 800 (FIG. 12a) through heating the stent to 105° C. for 60 minutes and holding in a conventional mandrel to form the first configuration (FIG. 12a).

The pigtails 804 and 805 on the stent are partally straightened or uncoiled to 270° and surface coated with a hydrogel polyvinylpyrrolidone, polyvinylalcohol, or polyethyleneoxide which was allowed to harden and hold the stent 800 in a second configuration (FIG. 12b) to form connecting section extensions 806 and 807. Upon hydration (FIG. 12c), the connecting section 801 and the end sections 802 and 803 of the stent 800 expanded in length and diameter due to the hydration of the hydrophilic polymer in the interpenetrating network. Moreover, the hydrogel on the connecting section extensions 806 and 807 dissolved away, recoiling the pigtails to their first configuration of 540°.

As will be appreciated, the first configuration allowed easy insertion of the stent 800 into a ureter in a patient since the 270° coils could be easily straightened over a guidewire yet assist in retaning the stents position on insertion. Further, the expansion (of both diameter and length of the connecting section 801) allowed for good flow through the ureter and kept the stent 800 at a constant length even with the recoiling of the pigtails 804 and 805.

Example 2

Preparation of a Shape Memory Stent Utilizing an Interpenetrating Network Polymer System and Thermal Shaping In this example, a catheter is formed from an interpenetrating network polymer system including a hydrophilic and a non-hydrophilic polymer. In the interpenetrating network system, the hydrophilic polymer is utilized as the first polymer which acts to holds the second (non-hydrophilic polymer) in a desired conformation. Such desired conformation until such time as the catheter is contacted with a bodily fluid and the hydrophilic polymer within the interpenetrating network loses its mechanical strength. At that time, the catheter will revert to a shape dictated or allowed by the second non-hydrophilic polymer.

The catheter is formed as described in Example 1. The catheter is shaped into a urinary stent with a small radius (i.e., ¼ inch), multiple pigtail (i.e., 360° or greater) on each end as discussed in Example 1. The pigtails are formed using a forming temperature above the melting point of the hydrophilic component and below the melting point of the non-hydrophilic component. This forming temperature sets a pigtail shape in both components (referred to as the first configuration).

The urinary stent may then be reshaped to a larger radius (i.e., ½ inch), partial pigtail (i.e., less than or equal to 270°) and in some cases may be completely straightened on a new forming tool. As repositioned in this new shape, the stent has assumed the configuration. Generally, it is set in this shape using a temperature below the forming temperature of the non-hydrophilic component, but above the forming temperature of the hydrophilic component. The stent is then cooled in the second configuration for insertion into the body. The hydrophilic component holds the non-hydrophilic component in the second configuration.

During hydration (inside the body) the hydrophilic component loses its mechanical strength and becomes soft and flexible, thus allowing the non-hydrophilic component to resume its original shape (the first configuration) which has more coiling and a smaller radius and possibly a greater retention force and any geometry may be achieved.

Example 3

Preparation of a Shape Memory Stent Utilizing an Interpenetrating Network Polymer System and Hydration In Example 2, the stent was reformed from the first to the second configuration through heating the catheter to a temperature that would soften the hydrophilic component but does not soften the non-hydrophilic polymer. Typically, the temperature exceeds the forming temperature of the hydrophilic component. As an alternative to the use of heat to reform a polymeric device in accordance with the invention, it is also possible to use hydration followed by drying or hardening to lock the device into the second conformation.

In this embodiment, the same product configurations as in the above examples are used. However, rather than heating the stent to a temperature above the forming temperature of the hydrophilic component but below the forming temperature of the nonhydrophilic component and changing the configuration, the stent (in the first configuration) may be reshaped into the second configuration through hydrating the device and holding the hydrated device in a second configuration while it dries.

This embodiment is useful in situations where the melting of the hydrophilic component is not acceptable. For example, in certain situations, an excessively high melt temperature of the hydrophilic component could have undesirable effects on the non-hydrophilic component. In addition, excessive temperatures could cause an additive, in the hydrophilic component (such as a medicament or drug) to be degraded. Further, it is also possible to include medicaments or drugs in the aqueous solution that is used for hydration. Such drugs or medicaments can be taken up by the hydrophilic component, retained while it is dry or hardened, and released upon insertion or implantation into a patient.

Example 4

Preparation of a Shape Memory Intraocular Lens

In another embodiment, an intraocular lens (IOL) is fabricated from a shape memory polymer, including an interpenetrating network, in accordance with the present invention. In such embodiment, the IOL can be formed into a folded position (as the second configuration) from its open conformation (as the first configuration) prior to insertion into a patient. The second configuration allows a smaller incision to be made into the patient's eye, and, reduces trauma.

The triggering event for the conversion from the second configuration of the IOL to the first configuration of the IOL may be selected from any of a variety of events. For example, a temperature sensitive polymer may be used to form the lens. In such embodiment, when the IOL is inserted and upon reaching body temperature the IOL would reform from the folded (second configuration) to into the unfolded (first configuration) shape. Thus, the IOL will be in a configuration for remaining in position in the patient's eye and correcting his or her vision in a manner similar to that described in Stoy U.S. Pat. No. 4,731,079.

Example 5

Preparation of a Shape Memory Intraocular Lens

In the Stoy patent, a disadvantage to heat trigger approach is evident. It is likely that temperatures, higher than body temperatures, will be experienced by the IOL during the shipping and/or storage of this device. Therefore, the patent taught that it was necessary to store the device in a clamped position within its packaging and to cool the device prior to insertion. Alternatively, the IOL could be fabricated on-site so that temperatures could be controlled. Either of these approaches add a great deal of complexity to the procedure.

These limitations are also applicable in connection with the IOL disclosed in connection with Example 4. Therefore, in this example, another shape memory approach that is relatively insensitive to temperature is provided. Such approach eliminates much of the complexity described above. In the procedure, the IOL is coated, either through a surface coating or through use of an interpenetrating network, with a hydrophilic polymer that is stiff/rigid when dry or hardened, and will not soften at temperatures experienced during shipping and storage.

For surface coating applications, one appropriate hydrophilic polymer is polyvinyl pyrrolidone (PVP) which is biocompatible and has been used in the eye, and would not melt at temperatures below 90° C. (195° F.). After IOL is processed appropriately, and pre-folded, the IOL could be dipped into a liquid solution of PVP and dried. Once placed within the body, the body fluids would dissolve the PVP, and allow the IOL to resume the shape upon reaching body temperature.

Example 6

Preparation of a Shape Memory Catheter

In this embodiment, virtually any catheter which includes an internal lumen may be provided with shape memory properties through the coating of the internal lumen with a dissolvable layer, such as a hydrogel. Several advantages are conferred by surface coating with a dissolvable material within the internal lumen. For example, a very low profile catheter can be used, since the coating will be internal. As the coating is dissolvable, the coating will dissolve and will be free to flow from (or otherwise be removed from the lumen) upon hydration/dissolution of the coating and the lumen will be open. A non-dissolvable coating can also be used (such as an interpenetrating network), however, the lumen will not open as it would with a dissolvable coating.

A catheter with the hydratable material in the internal lumen will behave in a similar manner as the devices discussed in Examples 1–3.

It is also possible to use the internal dissolvable coating approach for the preparation of low profile catheters with initial high pushability, followed by extreme flexibility. This is accomplished in accordance with the invention through the fact that a hydrogel (or other dissolvable polymer) can be utilized to hold the catheter in a initial fixed or rigid conformation (such as straight). Such rigid conformation will be easily advanced through a duct or vasculature in a patient. As the dissolvable layer is contacted with bodily fluids the catheter will lose some of its rigidtiy and will increase in flexibility. These aspects are advantageous for urethral, uretal, and cardiovascular applications.

As was mentioned above, while certain of these shape memory features can be obtained through the use of heat triggers (features such as longitudinal stretching and folded-in reduced diameter catheters (i.e., Fuqua U.S. Pat. No. 4,710,818)), heat sensitive polymers pose the problem of premature release. Therefore, by coating the inner lumen with a hydrogel, the device is held in its proper shape until fluid flow through the lumen begins and softens the hydrogel thereby allowing the device to change shape or rigidity.

In the case of urethral and uretal catheters, it is desirable to have sufficient working time to place the catheter far enough through the urethra to allow flow from the bladder to begin before the shape changes. This is very important and beneficial in the case of pediatric urethral catheters which are usually so small that the flow through the tube is especially slow, but cannot be made faster by a larger tube due to size constraints of the child's urethra. Additionally, a stiffer/smaller tube can be inserted which will soften considerably for patient comfort once the hydrogel has softened.

Example 7

Preparation of Shape Memory Catheter

Another example of a shape memory catheter in which a first material holds a second material until the first material is hydrated inside the body again uses the principle of coating catheters to hold them in different configurations.

In this example, a conventional urinary stent prepared from silicone, polyurethane, or another suitable material may be shaped with pigtails at each end as described in Example 1. This catheter configuration including the pigtails is in the first configuration. The catheter may then be straightened partially or completely on a rod and coated with a hydrophilic polymer. The hydrophilic polymer after drying, curing, or hardening will hold the urinary stent straight or partially straight in the second configuration. Upon hydration (inside the body), the hydrophilic polymer loses its mechanical strength and allows the coated material in the catheter to return to its initial formed shape, the first configuration. Moreover, since the catheter will be pre-stressed through its deformation into the first configuration, greater coil retention force may be possible.

Example 8

Preparation of a Nonexpanding Interpenetrating Network Shape Memory Stent

Another example includes a bIliary stent prepared using an interpenetrating network. As will be appreciated, when an interpenetrating network is utilized in a device, such as a stent or a catheter, the hydrophilic component acts to cause the device to expand. In the case of a tubular device, such as a stent or a catheter, expansion may occur both radially and longitudinally. Longitudinal expansion is sometimes not desirable.

Therefore, in order reduce or eliminate longitudinal expansion (or to attain zero length swell), the tube including the interpenetrating network is heated to a temperature above the melting point of the hydrophilic component, but below the relative transition temperature of the non-hydrophilic compound and stretched to a particular new length. The new length is chosen based upon expected longitudinal expansion of the interpenetrating network upon hydration and cooled at this new length.

The hydrophilic component, then, will act to hold the non-hydrophilic component at this new length. Upon hydration, the hydrophilic component loses its ability to hold the non-hydrophilic component in this stressed position, and the non-hydrophilic component would tend to snap back in length. However, concurrently the hydrophilic component is not only losing its ability to hold the other component, but it is expanding and beginning to hold the other component in this stretched position by means of its expansion force. This balance of softening/shrinking versus swelling/stretching is balanced for an effective length change that is negligible.

Therefore, the use of prestretching acts to counteract longitudinal expansion of the interpenetrating network.

Example 9

Preparation of a Nonexpanding Interpenetrating Network Shape Memory Nephrostomy Catheter A nephrostomy catheter formed from an interpenetratmg network may be prepared to maintain zero length swell using the same technique as that used for the bilary stent in Example 8. The nephrostomy catheter would be held with the hydrophilic material in a prestretched position. Upon hydration the hydrophilic material would lose its ability to hold the non-hydrophilic component to allow for the accommodating length swell during hydration.

Example 10

Preparation of a Nonexpanding Interpenetrating Network Shape Memory Nephrostomy Catheter

Another example includes a nephrostomy catheter formed from an interpenetrating network which includes a hydrophilic component and a non-hydrophilic component. The nephrostomy catheter is shaped with a coil on one end through heating the catheter to a forming temperature above the relative transition temperature of the non-hydrophilic component and above the melting point of the hydrophilic component and then cooled in that configuration, the first configuration. The nephrostomy catheter is then straightened for ease of insertion on a rod and raised to a temperature above the melting point of the hydrophilic component, but below the relative transition temperature of the non-hydrophilic component and cooled in that configuration, the second configuration.

Upon hydration, the nephrostomy catheter will return to its initial shape (the first configuration), since the hydrophilic component becomes soft and flexible and loses its mechanical strength and ability to hold the non-hydrophilic component straight in the second configuration.

Example 11

Thermally Triggered Shape Memory Devices

Devices, such as ureteral stents, which have retention mechanisms such as pigtails, coils, multicoils, etc., usually must have the retention means straightened in order for the stent to be placed onto a guide wire that is already in the body. For example, often, pigtails, as described above, are used as retention means. A physician is faced with a couple of choices. Either he or she doctor must manually straighten the retention means out, which can be difficult to do when the stent material is stiff, or certain straighteners can be used. In the case of pigtails, certain devices are pre-packaged with coaxial "pigtail straighteners" which is a tube that is stiffer than the stent material and is advanced by the surgeon over the "Pigtail" to straighten the "Pigtail" and allow a guide wire to be placed inside the straight pigtail. The Pigtail straightener is then slid to the other end and the guide wire is further advanced into the other Pigtail. This pigtail straightener is then thrown away.

In order to avoid these difficulties, however, a stent can be formed from a two component tube (i.e., an interpenetrating network, described above, or from coaxial layers). The bulk of the device would be made of a material with sufficient strength to act as a functional ureteral stent (Pellethane or Tecoflex). The balance of the device would be made of a thermally sensitive material that would lose its strength and/or change shape at body temperature.

A device can be manufactured in this manner and formed into a first conformation. For example, a ureteral stent having pigtails. The stent is then straightened to provide the second conformation. The thermally sensitive material would hold the other polymer straight to allow a straight stent to be passed over the guide wire. Once over the wire and in place in the body and at body temperature, the thermally sensitive material would allow the pigtails to form.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

That which is claimed is:

1. A polymeric medical device designed for internal use in a patient, comprising a polymer structure that would ordinarily assume a first conformation and a hydrophilic polymer coated upon at least a portion of the structure, the hydrophilic polymer being in a second conformation and having sufficient rigidity such that the polymer structure is held in the second conformation, wherein upon hydration of the hydrophilic polymer the polymer structure assumes the first conformation.

2. The medical device of claim 1, wherein the hydrophilic polymer is selected from the group consisting of poly (ethylene oxide), polyvinyl pyrrolidone, polyvinyl alcohol, poly(ethylene glycol), polyacrylamide, poly (hydroxy alkyl methacrylates), poly(hydroxy ethyl methacrylate), hydrophilic polyurethanes, HYPAN, oriented HYPAN, poly (hydroxy ethyl acrylate), hydroxy ethyl cellulose, hydroxy propyl cellulose, methoxylated pectin gels, agar, starches, modified starches, alginates, hydroxy ethyl carbohydrates and mixtures and copolymers thereof.

3. The medical device of claim 1, wherein the hydrophilic polymer, upon hydration, softens and expands by from about 5% to about 300%.

4. The medical device of claim 1, wherein the polymer structure comprises an interpenetrating network.

5. A polymeric medical device designed for internal use in a patient, comprising a polymer structure, the polymer structure comprising a first polymer material preconfigured into a first conformation and a second hydrophilic polymer material preconfigured into a second conformation, the first and second polymers having respective mechanical strengths, the mechanical strength of the second polymer material exceeding that of the first polymer material sufficiently so that the polymer structure is in the second conformation, wherein the second polymer material is adapted to lose its mechanical strength upon the occurrence of a triggering event and upon loss of the mechanical strength of the second polymer, the device assumes the first conformation.

6. The medical device of claim 5, wherein the hydrophilic polymer is selected from the group consisting of poly (ethylene oxide), polyvinyl pyrrolidone, polyvinyl alcohol, poly(ethylene glycol), polyacrylamide, poly (hydroxy alkyl methacrylates), poly(hydroxy ethyl methacrylate), hydrophilic polyurethanes, HYPAN, oriented HYPAN, poly (hydroxy ethyl acrylate), hydroxy ethyl cellulose, hydroxy propyl cellulose, methoxylated pectin gels, agar, starches, modified starches, alginates, hydroxy ethyl carbohydrates and mixtures and copolymers thereof.

7. The medical device of claim 6, wherein the triggering event is hydration of the second polymer material.

8. The medical device of claim 5, wherein the triggering event is an increase in temperature.

9. The medical device of claim 5, wherein the hydrophilic polymer, upon hydration, softens and expands by from about 5% to about 300%.

10. The medical device of claim 5, wherein the first polymer comprises an interpenetrating network.

11. The medical device of claim 5, wherein the polymer structure comprises an interpenetrating network.

\* \* \* \* \*